US011000181B2

(12) United States Patent
Ohno

(10) Patent No.: US 11,000,181 B2
(45) Date of Patent: May 11, 2021

(54) ENDOSCOPE CAMERA HEAD

(71) Applicant: Sony Olympus Medical Solutions Inc., Tokyo (JP)

(72) Inventor: Atsuomi Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 554 days.

(21) Appl. No.: 15/903,057

(22) Filed: Feb. 23, 2018

(65) Prior Publication Data

US 2018/0263471 A1 Sep. 20, 2018

(30) Foreign Application Priority Data

Mar. 17, 2017 (JP) .............................. JP2017-053416

(51) Int. Cl.
| | |
|---|---|
| *A61B 1/00* | (2006.01) |
| *A61B 1/05* | (2006.01) |
| *A61B 1/04* | (2006.01) |
| *G02B 23/24* | (2006.01) |
| *A61B 1/06* | (2006.01) |

(52) U.S. Cl.
CPC ...... *A61B 1/00105* (2013.01); *A61B 1/00039* (2013.01); *A61B 1/00066* (2013.01); *A61B 1/00174* (2013.01); *A61B 1/042* (2013.01); *A61B 1/05* (2013.01); *G02B 23/2484* (2013.01); *A61B 1/0008* (2013.01); *A61B 1/0011* (2013.01); *A61B 1/00126* (2013.01); *A61B 1/0661* (2013.01)

(58) Field of Classification Search
CPC ............ A61B 1/00039; A61B 1/00066; A61B 1/0066; A61B 1/042
See application file for complete search history.

(56) References Cited

U.S. PATENT DOCUMENTS

| 2005/0267329 A1* | 12/2005 | Konstorum ........ A61B 1/00101 600/112 |
| 2007/0070340 A1* | 3/2007 | Karpen .................. A61B 1/053 356/241.1 |

(Continued)

FOREIGN PATENT DOCUMENTS

| JP | 2012-245045 | 12/2012 |
| JP | 2016-214661 A | 12/2016 |

OTHER PUBLICATIONS

Office Action dated Dec. 8, 2020, in Japanese Patent Application No. 2017-053416, 4 pages.

*Primary Examiner* — Aaron B Fairchild
(74) *Attorney, Agent, or Firm* — Xsensus LLP

(57) ABSTRACT

An endoscope camera head includes: a main body unit having an irregular tubular shape made of a metal or an alloy and including a hollow portion that is airtightly concealed; an imaging unit accommodated in the hollow portion of the main body unit and configured to generate an image signal based on light from an object; and an operating unit configured to output an operation signal for operating the imaging unit. The operating unit includes an input unit located at a position extending over a first face and a second face adjacent each other, of a surface of the main body unit, and configured to receive an input of the operation signal from an outside, and a fixing unit configured to fix the input unit to the main body unit.

8 Claims, 5 Drawing Sheets

(56) References Cited

U.S. PATENT DOCUMENTS

| | | | | |
|---|---|---|---|---|
| 2007/0219409 A1* | 9/2007 | Shimizu | ............ | A61B 1/00039 600/112 |
| 2007/0276183 A1* | 11/2007 | Melder | ............ | A61B 1/00128 600/112 |
| 2014/0100424 A1* | 4/2014 | Hoshino | ............ | A61B 1/00039 600/118 |

* cited by examiner

ENDOSCOPE CAMERA HEAD

CROSS-REFERENCE TO RELATED APPLICATION

The present application claims priority to and incorporates by reference the entire contents of Japanese Patent Application No. 2017-053416 filed in Japan on Mar. 17, 2017.

BACKGROUND

The present disclosure relates to an endoscope camera head.

In the related art, camera heads that are imaging devices for endoscopes that are inserted into a subject and capture an inside of the subject are known. A lens unit and an imaging element are accommodated inside the camera head. A camera head for medical use needs to reliably prevent inflow of a gas into the inside of the camera head so that autoclave sterilization may be performed in a high-temperature and high-pressure atmosphere.

For example, JP 2012-245045 A discloses a camera head provided with an airtight casing capable of preventing inflow of a gas, a button portion provided outside the airtight casing and for which an operation input is performed, and a tubular exterior member from which the button portion protrudes and covering an outer periphery of the airtight casing.

SUMMARY

The camera head in JP 2012-245045 A described above has a double structure of the airtight casing and the exterior member, and the configuration is complicated.

An endoscope camera head according to one aspect of the present disclosure may include: a main body unit having an irregular tubular shape made of a metal or an alloy and including a hollow portion that is airtightly concealed; an imaging unit accommodated in the hollow portion of the main body unit and configured to generate an image signal based on light from an object; and an operating unit configured to output an operation signal for operating the imaging unit, and the operating unit may include an input unit located at a position extending over a first face and a second face adjacent each other, of a surface of the main body unit, and configured to receive an input of the operation signal from an outside, and a fixing unit configured to fix the input unit to the main body unit.

DETAILED DESCRIPTION

Figure 1:
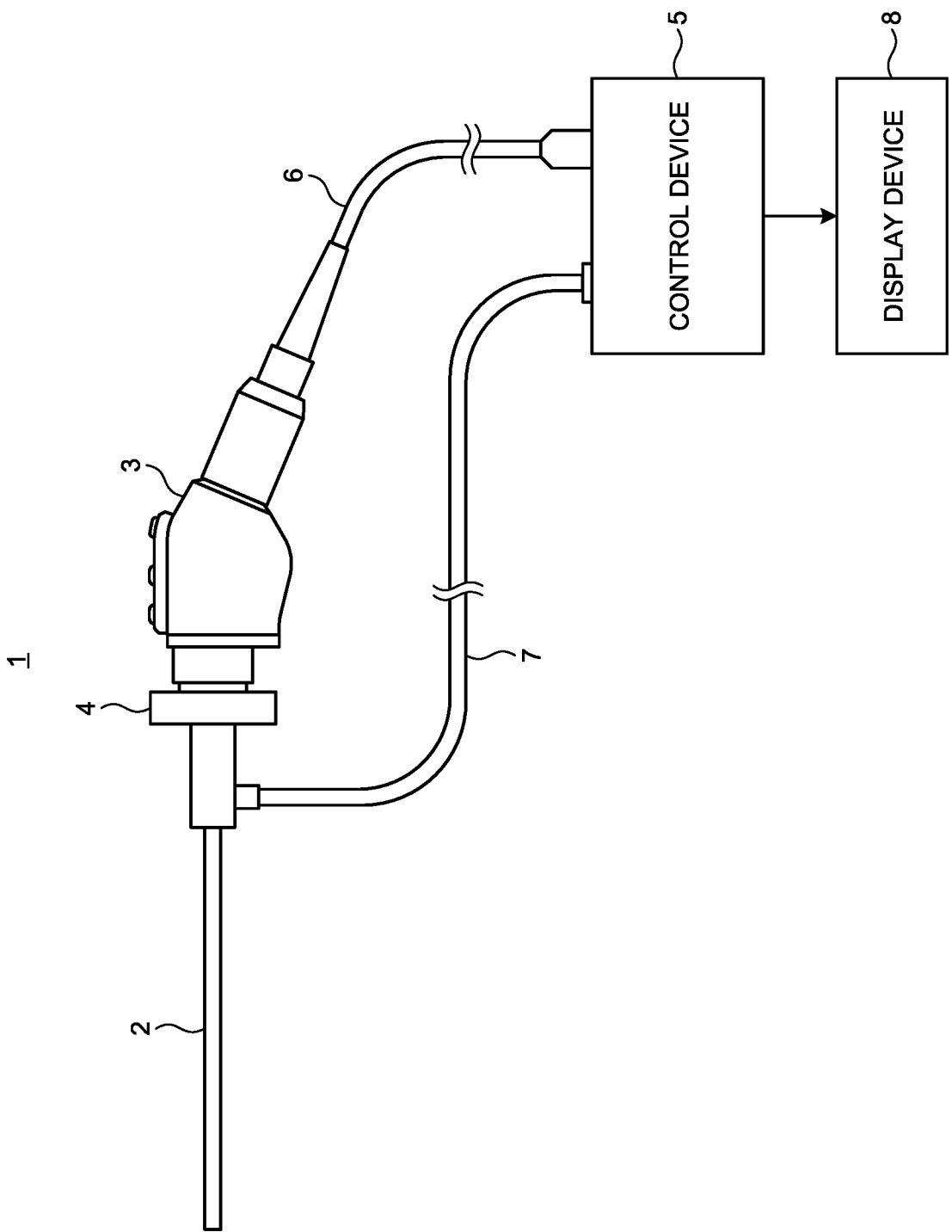
FIG. 1 is a diagram illustrating a schematic configuration of a medical endoscope system including an endoscope camera head according to an embodiment.

Hereinafter, an embodiment will be described with reference to the accompanying drawings. The same portions are denoted with the same sign in the illustration of the drawings. Note that the drawings are schematic, and dimensions of the same portions and ratios of sizes between the same portions in the drawings may be different in some cases.

FIG. 1 is a diagram illustrating a schematic configuration of a medical endoscope system including an endoscope camera head according to an embodiment. A medical endoscope system 1 illustrated in FIG. 1 includes: a rigid endoscope 2 that is an endoscope having a distal end portion inserted into a living body, and condenses light in the living body and illuminates an inside of the living body; a camera head 3 that is an endoscope camera head that captures the light from the living body condensed by the rigid endoscope 2 and generates an image signal; a connecting portion 4 mounted to the camera head 3 on a proximal end side and which detachably connects the rigid endoscope 2 on the distal end side; a control device 5 that controls an operation of the camera head 3 and generates illumination light to be supplied to the rigid endoscope 2; a transmission cable 6 that connects the camera head 3 and the control device 5 and transmits an electrical signal and the like; a light guide cable 7 that connects the rigid endoscope 2 and the control device 5 and propagates the illumination light generated by the control device 5 to the rigid endoscope 2; and a display device 8 connected to the control device 5, and which displays information such as an image generated by the camera head 3.

Figure 2:
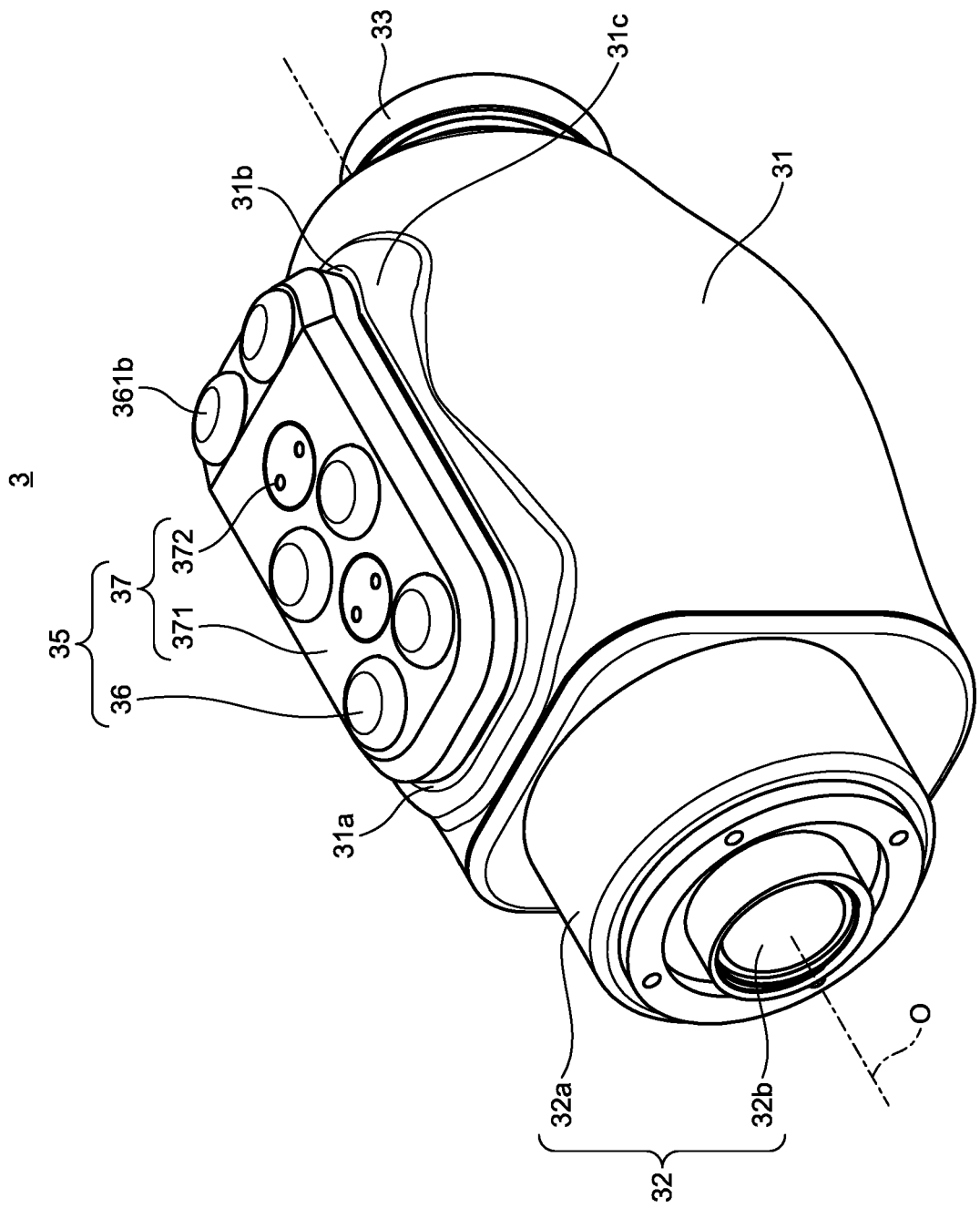
FIG. 2 is a perspective view illustrating a configuration of an endoscope camera head according to an embodiment.
Figure 3:
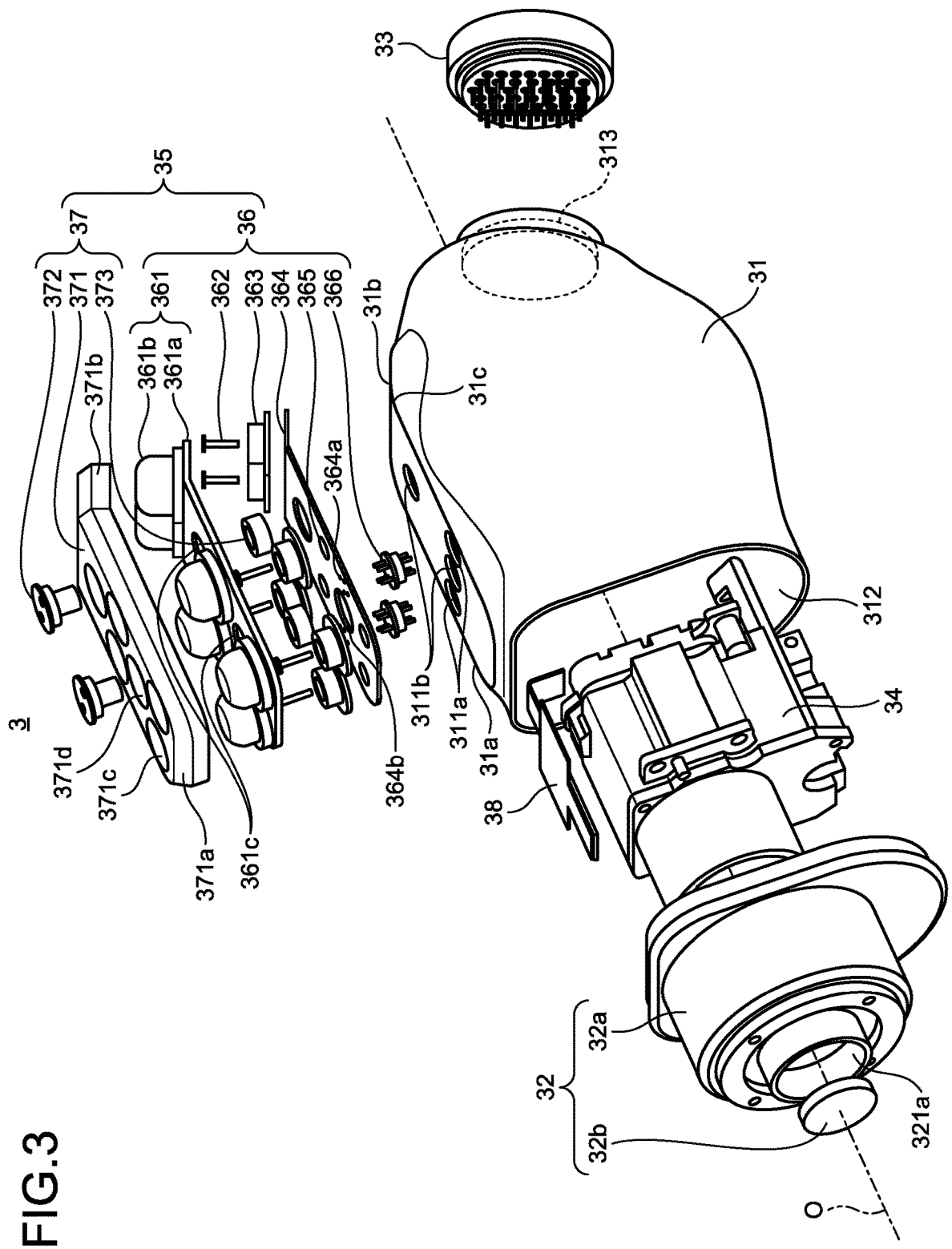
FIG. 3 is an exploded perspective view illustrating a configuration of an endoscope camera head according to an embodiment.
Figure 4:
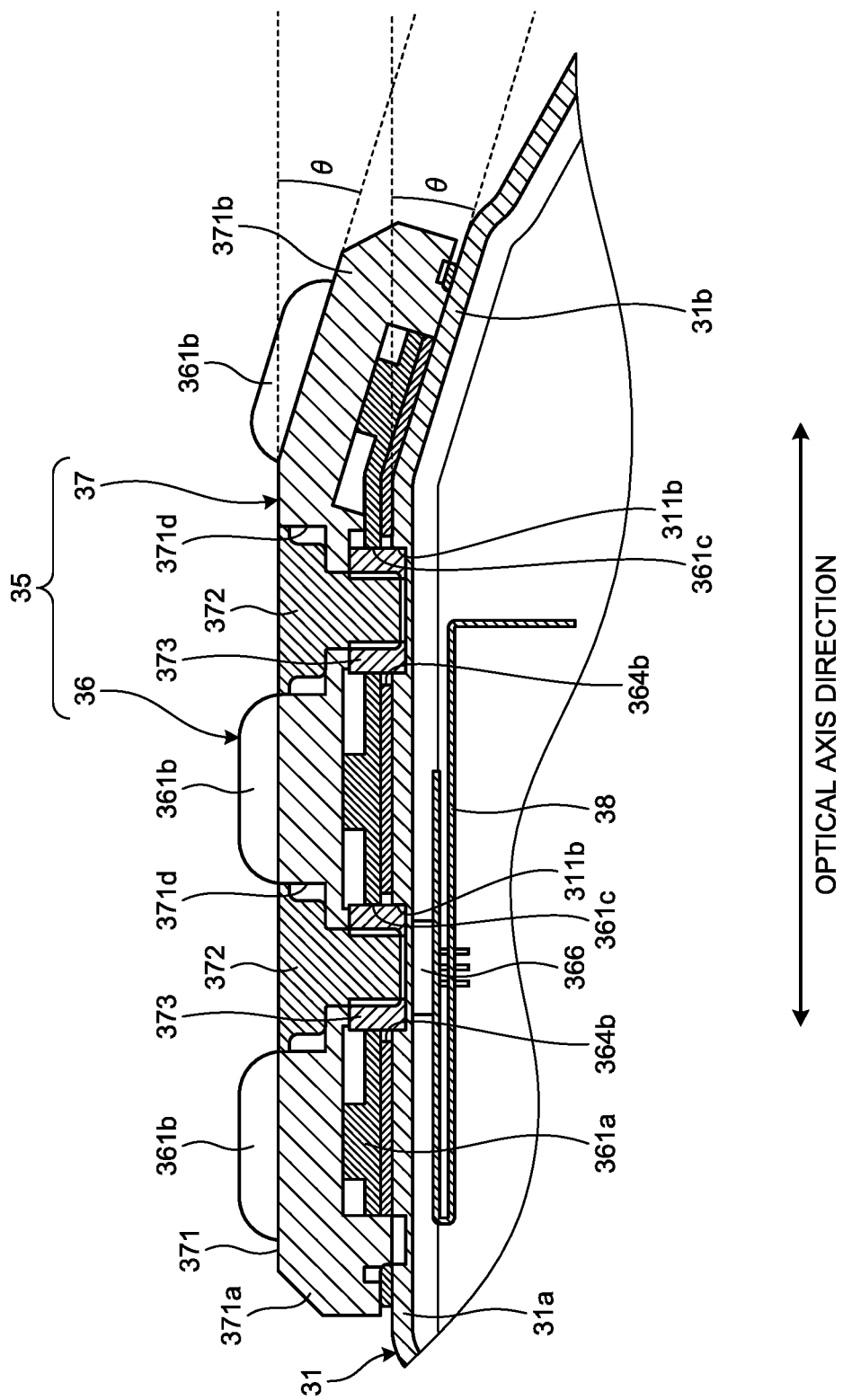
FIG. 4 is a partial sectional view illustrating a configuration of an operating unit included in an endoscope camera head according to an embodiment.

FIG. 2 is a perspective view illustrating a configuration of the camera head 3. FIG. 3 is an exploded perspective view illustrating the configuration of the camera head 3. FIG. 4 is a partial sectional view illustrating a configuration of an operating unit included in the camera head 3. Hereinafter, the configuration of the camera head 3 will be described with reference to FIGS. 2 to 4.

The camera head 3 includes a main body unit 31 formed into an irregular tubular shape formed using a metal or an alloy, a cover unit 32 that conceals a first opening portion 312 that is an opening portion on a side connected with the rigid endoscope 2, of opening portions formed in the main body unit 31, and is fixed to the main body unit 31, a connector unit 33 that conceals a second opening portion 313 that is an opening portion on a side connected with the transmission cable 6, of opening portions formed in the main body unit 31, and is fixed to the main body unit 31, an imaging unit 34 accommodated in the main body unit 31, and including an optical system that condenses light condensed by the rigid endoscope 2 and an imaging element that generates an image signal based on the light condensed by the optical system, and an operating unit 35 that outputs various signals including an operation signal for operating the imaging unit 34 to the main body unit 31. Hereinafter, the side provided with the cover unit 32 is referred to as distal end side, and the side provided with the connector unit 33 is referred to as proximal end side. The "irregular shape" referred here means a shape formed taking into consideration of ease of gripping by a human hand, and more specifically, a shape having a curved face comfortably fit in a user's hand when the user holds the camera head 3.

A surface of the main body unit 31 includes a first face 31a that is a plane approximately parallel to an optical axis O of the imaging unit 34, a second face 31b that is a plane located on the proximal end side with respect to the first face 31a, adjacent to the first face 31a, inclined with respect to the first face 31a, and approaching the optical axis O of the imaging unit 34 as away from the first face 31a along the optical axis O of the imaging unit 34, and a curved face 31c lying between the first face 31a and the second face 31b, and smoothly connected with the first face 31a and the second face 31b. The main body unit 31 is configured from a hard metal such as titanium or stainless steel or an alloy containing such a metal. Note that the optical axis O of the imaging unit 34 is an optical axis of the optical system included in the imaging unit 34. Further, the first face 31a and the second face 31b may not be planes.

The first face 31a is provided with two hermetic connector accommodating portions 311a that respectively accommodate two hermetic connectors 366 (described below) included in the operating unit 35, and two nut accommodating portions 311b that respectively accommodate two nuts 373 (described below) included in the operating unit 35. Opening portions penetrating the first face 31a are formed in the hermetic connector accommodating portion 311a. The opening portions are airtightly concealed by welding the hermetic connectors 366. The nut accommodating portion 311b is a bottomed counterbored hole drilled by a counter boring process or the like. The nuts 373 accommodated in the nut accommodating portions 311b are fixed by welding. In the case illustrated in FIG. 3, the two hermetic connector accommodating portions 311a are aligned in the first face 31a in a direction orthogonal to the optical axis O of the imaging unit 34, and one nut accommodating portion 311b is formed therebetween. The other nut accommodating portion 311b is located closer to the proximal end side than the nut accommodating portion 311b located between the two hermetic connector accommodating portions 311a. The two nut accommodating portions 311b are aligned along a direction (optical axis direction) parallel to the optical axis O of the imaging unit 34. Note that the numbers of the hermetic connector accommodating portions 311a and the nut accommodating portions 311b illustrated in FIG. 3 are merely an example and may be appropriately changed. Further, the hermetic connector accommodating portions may be formed in the second face 31b.

Two opening portions are formed in the main body unit 31. The cover unit 32 is welded to the first opening portion 312 formed on the distal end side. The connector unit 33 is welded to the second opening portion 313 formed on the proximal end side. The first opening portion 312 is airtightly concealed by the cover unit 32, and the second opening portion 313 is airtightly concealed by the connector unit 33. Further, the opening portions formed in the hermetic connector accommodating portion 311a are airtightly concealed by the hermetic connectors 366. As described above, all the opening portions formed in the main body unit 31 are airtightly concealed, and thus inflow of a gas from an outside into the hollow portion of the main body unit 31 is completely prevented and airtightness is secured.

The cover unit 32 includes a tubular cover member 32a, and a cover glass 32b attached in an opening portion 321a formed in the cover member 32a on the distal end side and to the opening portion 321a that the optical axis O of the imaging unit 34 passes through. The cover member 32a is formed using the same metal or alloy as the main body unit 31. The cover glass 32b is made of sapphire, for example, and airtightly conceals the opening portion 321a by having an outer edge portion soldered to the opening portion 321a. A proximal end side of the cover unit 32 is welded to the first opening portion 312 of the main body unit 31. As a result, the cover unit 32 prevents inflow of a gas into the hollow portion of the main body unit 31 through the first opening portion 312, and airtightly conceals the first opening portion 312.

The connector unit 33 is welded to the second opening portion 313 of the main body unit 31. The connector unit 33 is made of a hermetic connector in which surroundings of the conducting pins are filled with metalized glass or the like. The connector unit 33 prevents inflow of a gas into the hollow portion of the main body unit 31 through the second opening portion 313, and airtightly conceals the second opening portion 313.

As illustrated in FIG. 3, the imaging unit 34 is an integrated casing-like unit. Inside the unit, the optical system, the imaging element, and a control circuit that controls drive of the imaging element are provided. As described above, airtightness in the hollow portion of the main body unit 31 that accommodates the imaging unit 34 is secured. Therefore, even if autoclave sterilization processing is performed for the camera head 3, the imaging unit 34 is not affected.

The operating unit 35 is located to extend over the first face 31a and the second face 31b, and includes an input unit 36 that receives an input of an operation signal of the imaging unit 34 by pressing from an outside, and a fixing unit 37 that fixes the input unit 36 to the main body unit 31. The operating unit 35 and the main body unit 31 are watertightly concealed.

The input unit 36 includes an input key 361, a plurality of input pins 362, a plurality of guide members 363, a flexible substrate 364, a plurality of switches 365, and a plurality of hermetic connectors 366. The numbers of the input pins 362, the guide members 363, and the switches 365 are the same, and the three members constitute one set.

The input key 361 includes a base portion 361a having a plate shape following a shape of an upper surface of the main body unit 31 from the first face 31a to the second face 31b, and a plurality of protruding portions 361b protruding outward from the base portion 361a and respectively functioning as operation buttons. The input key 361 is configured from an elastic member. Two insertion holes 361c for allowing insertion of the nuts 373 are formed in the base portion 361a in positions respectively corresponding to the two nut accommodating portions 311b formed in the first face 31a of the main body unit 31 Part of the plurality of protruding portions 361b is located on the first face 31a, and the remaining protruding portions are located on the second face 31b. FIGS. 2 to 4 illustrate a case in which four protruding portions 361b are provided on the first face 31a and two protruding portions 361b are provided on the second face 31b. The number of the protruding portions 361b may be appropriately changed as long as the protruding portions 361b exist on the first face 31a and the second face 31b. Note that the protruding portion 361b may be disposed to pass through the curved face 31c.

The input pins 362, the guide members 363, the flexible substrate 364, the switches 365, and the hermetic connectors 366 are provided in a gap between the input key 361 having the above-described configuration and the first face 31a. The input key 361 prevent inflow of a liquid into the gap from an outside, and secures watertightness in the gap.

The input pin 362 is fixed in such a manner that a head portion provided in a proximal end portion of the input pin 362 is in contact with an inner peripheral surface of the protruding portion 361b. When the corresponding protruding portion 361b is deformed by force from an outside, the input pin 362 is moved from the protruding portion 361b toward the main body unit 31 with the deformation and is moved until the distal end portion comes in contact with the switch 365 provided on the surface of the flexible substrate 364. When the protruding portion 361b is returned to the original shape, the input pin 362 is also away from the switch 365 and is retreated.

The guide member 363 has a cylindrical shape and guides advance or retreat movement of the input pin 362 inserted in a hollow portion of the guide member 363 with respect to the main body unit 31. The guide member 363 is press-fit to an inner side of the protruding portion 361b, and holds the input pin 362 inserted in the hollow portion in an advanceable or retreatable manner between the guide member 363 and the protruding portion 361b.

The flexible substrate 364 has a shape bent to follow the surface shape of the main body unit 31 from the first face 31a to the second face 31b. The plurality of switches 365 is provided on the outer surface of the flexible substrate 364 in accordance with the positions where the distal ends of the plurality of input pins 362 reach by movement. A plurality of pin insertion holes 364a for allowing insertion of the plurality of conducting pins included in the hermetic connectors 366 and connecting the conducting pings with wiring inside the substrate is formed in positions where the hermetic connectors 366 are accommodated in the main body unit 31, of a portion of the flexible substrate 364, the portion being in contact with the first face 31a. Further, two nut insertion holes 364b for allowing insertion of the nuts 373 of the fixing unit 37 are formed in the flexible substrate 364.

The switches 365 are provided on the outer surface side of the flexible substrate 364 as described above. When the input pin 362 comes in contact with the switch 365 with deformation of the protruding portion 361b, the switch 365 becomes an on state, a current flows in a circuit including the switch 365 provided on the flexible substrate 364, and an operation signal based on the current is output. The six switches 365 respectively output different operation signals. As the operation signals, for example, there are a signal for instructing autofocus (AF) in a central portion of a screen, a signal for instructing movement of the optical system toward a near (short distance) side and a far (long distance) side in manual focus (MF), a signal arbitrarily set by a user, and the like.

The hermetic connector 366 is accommodated in the hermetic connector accommodating portion 311a formed in the first face 31a and fixed by welding. While the hermetic connector 366 is electrically connected to the flexible substrate 364 outside the main body unit 31, the hermetic connector 366 is electrically connected to the imaging unit 34 via a substrate 38 inside the main body unit 31. To be specific, while, in the hermetic connector 366, the conducting pin protruding outside the main body unit 31 is soldered to an electrode or the like of the flexible substrate 364, the conducting pin protruding inside the main body unit 31 is soldered to an electrode of the substrate 38. Similarly to the hermetic connector described above, surroundings of the conducting pins of the hermetic connector 366 are filled with metalized glass or the like, and the hermetic connector 366 airtightly conceals the plurality of insertion holes formed in the first face 31a. The hermetic connector 366 having the above configuration outputs an operation signal from the flexible substrate 364 to the substrate 38. Note that the hermetic connector 366 may be fixed to at least one of the first face 31a and the second face 31b.

The fixing unit 37 includes a pressing plate 371 that presses the base portion 361a of the input key 361 toward the main body unit 31, and two sets of bolts 372 and nuts 373 that are screwed to fix the pressing plate 371 to the main body unit 31.

The pressing plate 371 includes a first face upper portion 371a stacked on the base portion 361a on the first face 31a and pressing the base portion 361a, and a second face upper portion 371b stacked on the base portion 361a on the second face 31b and pressing the base portion 361a, and has a shape following the shape of the upper surface of the main body unit 31 from the first face 31a to the second face 31b. In the case illustrated in FIG. 4, an intersection angle made by a surface of the first face upper portion 371a and a surface of the second face upper portion 371b is equal to an intersection angle made by the first face 31a and the second face 31b (both angles are θ in FIG. 4). The pressing plate 371 is fixed to the main body unit 31 in a state of pressing at least an outer edge portion of the base portion 361a of the input key 361.

In the pressing plate 371, a plurality of first insertion holes 371c for allowing insertion of any of the plurality of protruding portions 361b included in the input key 361 to protrude to an outside, and two second insertion holes 371d for allowing insertion of the bolts 372 are formed. The diameter of the first insertion hole 371c is slightly smaller than the maximum diameter of the protruding portion 361b. Therefore, the protruding portion 361b is press-fit into the first insertion hole 371c from the main body unit 31 side. The second insertion hole 371d has a stepped hole shape with a large outside diameter and a small inside diameter, and the head portion of the bolt 372 is in contact with the stepped portion. FIGS. 2 to 4 illustrates the case where four first insertion holes 371c and two second insertion holes 371d are formed in the first face upper portion 371a and two first insertion holes 371c are formed in the second face upper portion 371b.

The pressing plate 371 is formed using a resin. Therefore, the pressing plate 371 may be easily matched with the shapes of the first face 31a and the second face 31b of the main body unit 31, and may be easily formed into the shape pressing the input key 361. The intersection angle made by the surface of the first face upper portion 371a and the surface of the second face upper portion 371b in a state where the pressing plate 371 is removed from the main body unit 31 may be made larger than the intersection angle θ made by the first face 31a and the second face 31b of the main body unit 31. In this case, the effect to press the input key 361 in fixing the pressing plate 371 to the main body unit 31 may be further enhanced, and the degree of close contact between the input key 361 and the main body unit 31 may be increased. Note that the pressing plate 371 may be formed using a metal or an alloy.

The bolt 372 has a screw portion to be screwed with the nut 373 and a head portion having a diameter larger than the diameter of the screw portion. The bolt 372 is screwed with the nut 373 in a state in which the head portion comes in contact with the stepped portion of the second insertion hole 371d of the pressing plate 371 and presses the pressing plate 371 against the main body unit 31. The nut 373 is accommodated in the nut accommodating portion 311b formed in the main body unit 31 and is fixed to the main body unit 31 by welding.

According to the embodiment described above, the operating unit 35 is provided to extend over the first face 31a and the second face 31b adjacent to each other, of the surface of the airtight main body unit 31, the airtightness may be secured with the simple configuration.

Further, according to the present embodiment, the operating unit 35 is provided to extend over the two adjacent faces (the first face 31a and the second face 31b) along the direction of the optical axis O of the imaging unit 34. Therefore, the number of the operation switches and the degree of freedom of layout may be increased while maintaining the shape easily held by the user. In addition, by increasing the number of operation switches, the degree of freedom of function assignment of the switches according to user's operation frequency or the like may also be increased.

Further, according to the present embodiment, the hermetic connectors 366 are provided on one surface (the first face 31a) of the main body unit 31. Therefore, the operation to electrically connect the conducting pins of the hermetic connectors 366 and the substrate 38 by soldering or the like is easy. In particular, in the present embodiment, the hermetic connectors 366 are attached to the first face 31a located closer to the first opening portion 312 that is an opening portion having a relatively large diameter, of the two opening portions of the main body unit 31. Therefore, a tool for soldering and fingers of a worker may be easily put into the hollow portion from the first opening portion 312 side. Therefore, the hermetic connectors 366 and the substrate 38 may be more easily wired.

Figure 5:
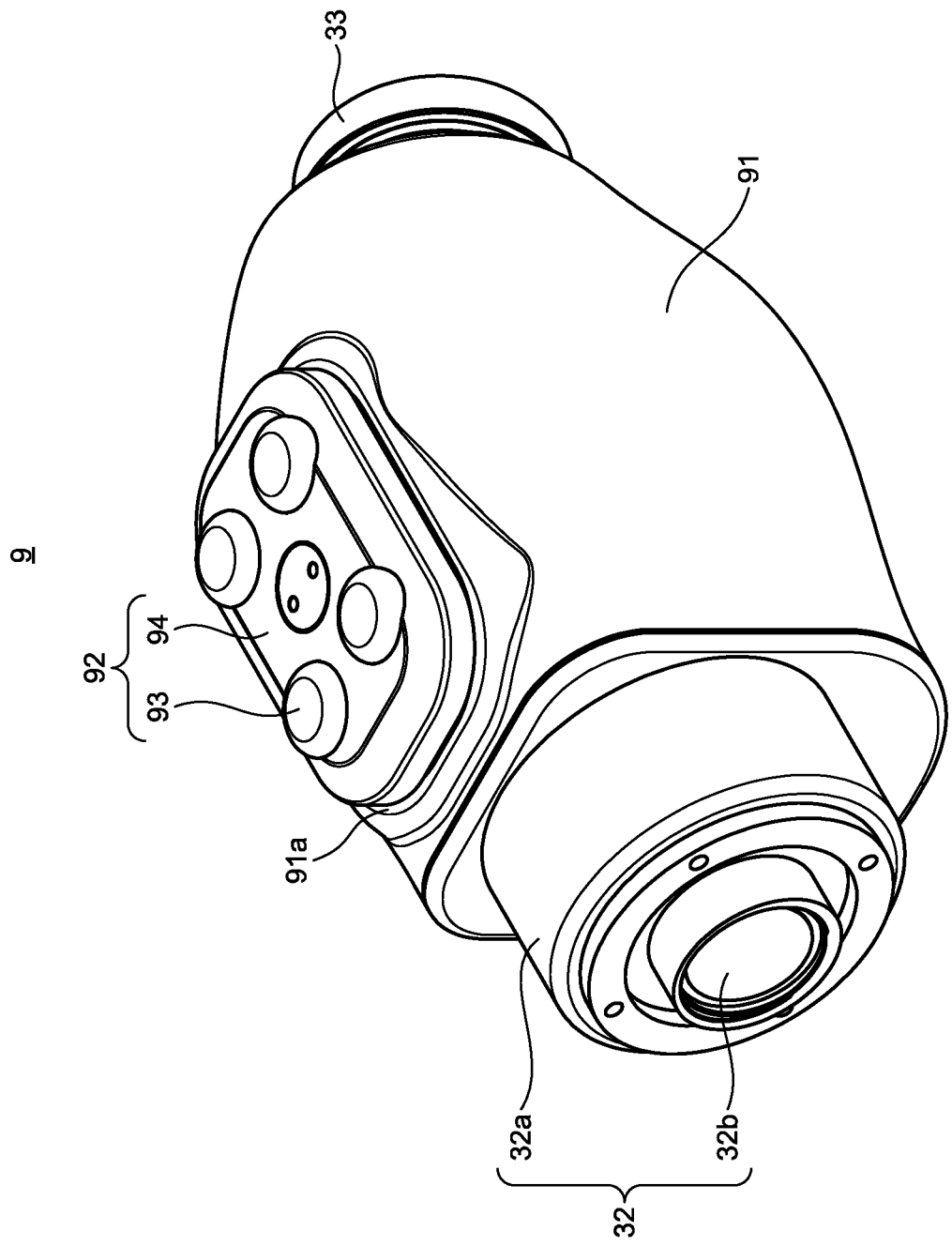
FIG. 5 is a perspective view illustrating a configuration of a conventional endoscope camera head.

Here, the effect of the present embodiment will be described while making a comparison with a conventional endoscope camera head illustrated in FIG. 5. A camera head 9 illustrated in FIG. 5 includes a main body unit 91, a cover unit 32, a connector unit 33, an imaging unit 34 (not illustrated) accommodated in the main body unit 91, and an operating unit 92. The operating unit 92 is provided on one plane 91a forming a part of a surface of the main body unit 91, and includes an input unit 93 and a fixing unit 94.

The camera head 9 is provided with the operating unit 92 on the one plane 91a and thus has a smaller number of protruding portions (four in the case illustrated in FIG. 5) than the camera head 3 provided with the operating unit 35 to extend over the two faces (the first face 31a and the second face 31b) of the main body unit 31.

In this regard, to increase the number of switches in the operating unit 92 on the one plane 91a, the area of the plane 91a needs to be increased by making the main body unit 91 large. However, if the main body unit 91 is made large, a problem that the camera head 9 becomes less easily held by the user occurs.

In contrast, in the present embodiment, the protruding portions 361b are provided over the two faces, and thus the number of the protruding portions 361b may be increased without changing the size of the main body unit 31. Therefore, the number of operation switches may be increased while maintaining easy grasp by the user.

Although the embodiment for carrying out the present disclosure has been described so far, the present disclosure should not be limited only by the above-described embodiment. For example, the operating unit may be provided on two faces adjacent in a direction going around the optical axis of the imaging unit instead of being provided on the two faces adjacent along the optical axis of the imaging unit, of the surface of the main body unit.

Further, one hermetic connector having a larger number of conducting pins and a larger diameter than the hermetic connector 366 may be fixed to the first face 31a, instead of using the two hermetic connectors 366. In the present embodiment, the operating unit is provided to extend over the two faces, and thus the attaching area of the operating unit may be sufficiently secured. Therefore, even a large hermetic connector may be applied to the operating unit. As a result, the number of parts may be reduced, cost reduction may be realized, and the configuration of the operating unit may be further simplified.

According to the present disclosure, airtightness may be secured with a simple configuration.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope camera head comprising:
a main body having an irregular tubular shape made of a metal or an alloy and including a hollow portion that is airtightly sealed;
a camera accommodated in the hollow portion of the main body and configured to generate an image signal based on light from an object; and
an operating panel to output an operation signal for operating the camera,
wherein the operating panel includes
an input panel that extends over a first face and a second face adjacent each other of the main body, the input panel being to receive an input of the operation signal from an outside, and
a pressing plate to fix the input panel to the main body the input panel including
a base that extends over the first face and the second face, and
a plurality of protrusions, each protrusion protruding outward from the base and being deformable, at least one protrusion being provided on each of the first face and the second face, wherein
the pressing plate is stacked on the base of the input panel and is fixed to the main body, pressing the base toward the main body,
the first face extends along an optical axis direction of the camera from a side of the main body receiving the light from an object, and
the second face is inclined with respect to the first face and approaches the optical axis direction of the camera.

2. The endoscope camera head according to claim 1, wherein the main body and the operating panel are watertightly sealed together.

3. The endoscope camera head according to claim 1, wherein the input panel includes
a hermetic connector fixed to at least one of the first face and the second face, electrically connected with the camera, and airtightly sealing the main body.

4. The endoscope camera head according to claim 3, wherein the hermetic connector is fixed to only one of the first face and the second face.

5. The endoscope camera head according to claim 3, further comprising:
a first cover airtightly sealing a first opening in the main body on a side of the main body where the camera receives the light from the object, the first cover to guide light condensed by an endoscope to the camera; and
a second cover airtightly sealing a second opening on a side of the main body where the camera outputs an image signal, the second cover electrically connecting the camera and an external transmission cable for transmitting the image signal, wherein
the hermetic connector is fixed to the first face.

6. The endoscope camera head according to claim 1, wherein
the first face and the second face are planar, and
the main body between the first face and the second face has a curved face smoothly connected with the first face and the second face.

7. The endoscope camera head according to claim 1, wherein the pressing plate includes a first upper face region stacked on the base on the first face and pressing the base, and a second upper face region stacked on the base on the second face and pressing the base, and an intersection angle made by a surface of the first upper face region and a surface of the second upper face region in a state where the pressing plate is removed is larger than an intersection angle made by the first face and the second face of the main body.

8. The endoscope camera head according to claim 5, wherein the second opening has a smaller diameter than the first opening.

* * * * *